United States Patent [19]

Somekh

[11] 4,013,640

[45] Mar. 22, 1977

[54] PROCESS FOR THE RECOVERY OF AMIDES

[75] Inventor: George S. Somekh, New Rochelle, N.Y.

[73] Assignee: Union Carbide Corporation, New York, N.Y.

[22] Filed: Apr. 11, 1974

[21] Appl. No.: 459,968

[52] U.S. Cl. .................. 260/239.3 A; 260/293.86; 260/326.5 FL; 260/326.5 FN; 260/561 R
[51] Int. Cl.² ..................................... C07D 201/16
[58] Field of Search ............... 260/239.3 A, 293.86, 260/326.5 FN, 561 A, 326.5 FL, 561 R

[56] References Cited

UNITED STATES PATENTS

| | | | |
|---|---|---|---|
| 3,359,260 | 12/1967 | Roberts et al. | 260/239.3 A |
| 3,904,609 | 9/1975 | Mattone et al. | 260/239.3 A |
| 3,912,721 | 10/1975 | Mattone et al. | 260/239.3 A |

FOREIGN PATENTS OR APPLICATIONS

| | | | |
|---|---|---|---|
| 896,883 | 5/1944 | France | 260/239.3 A |

Primary Examiner—Henry R. Jiles
Assistant Examiner—Robert T. Bond
Attorney, Agent, or Firm—Marylin Klosty

[57] ABSTRACT

A solvent extraction-distillation process for the recovery of a water-soluble aliphatic amide having 1 to 8 carbon atoms or mixtures thereof from an aqueous solution wherein the concentration of the amide is in the range of about 0.25 percent by weight to about 25 percent by weight, based on the weight of the solution, and the solvent is a compound having the following structural formula:

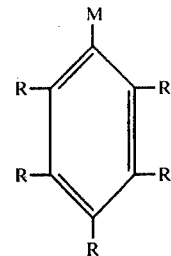

wherein M is OH or $CH_2OH$, R is hydrogen or an alkyl radical, there being at least one alkyl radical, and the total number of carbon atoms in all of said alkyl radicals taken together is 3 to 12, or a mixture of isomers thereof, said compound or mixture of isomers having a boiling point higher than the amide and less than about 350° C. and being non-azeotropic with the amide, comprising the following steps:

(a) contacting the solution in an extraction zone with the solvent to provide an extract comprising solvent, amide, and no more than about 5 percent by weight of water based on the weight of the solution and a raffinate comprising at least about 95 percent by weight of water based on the weight of the solution and less than about 5 percent by weight of solvent based on the weight of the solvent;

(b) introducing the extract from step (a) into a distillation zone wherein the pressure is less than about 500 millimeters of mercury and the temperature is less than the decomposition temperatures of the amide and the solvent at said pressure, to separate the solvent from a mixture of amide and water; and (c) recovering the mixture of amide and water.

10 Claims, 1 Drawing Figure

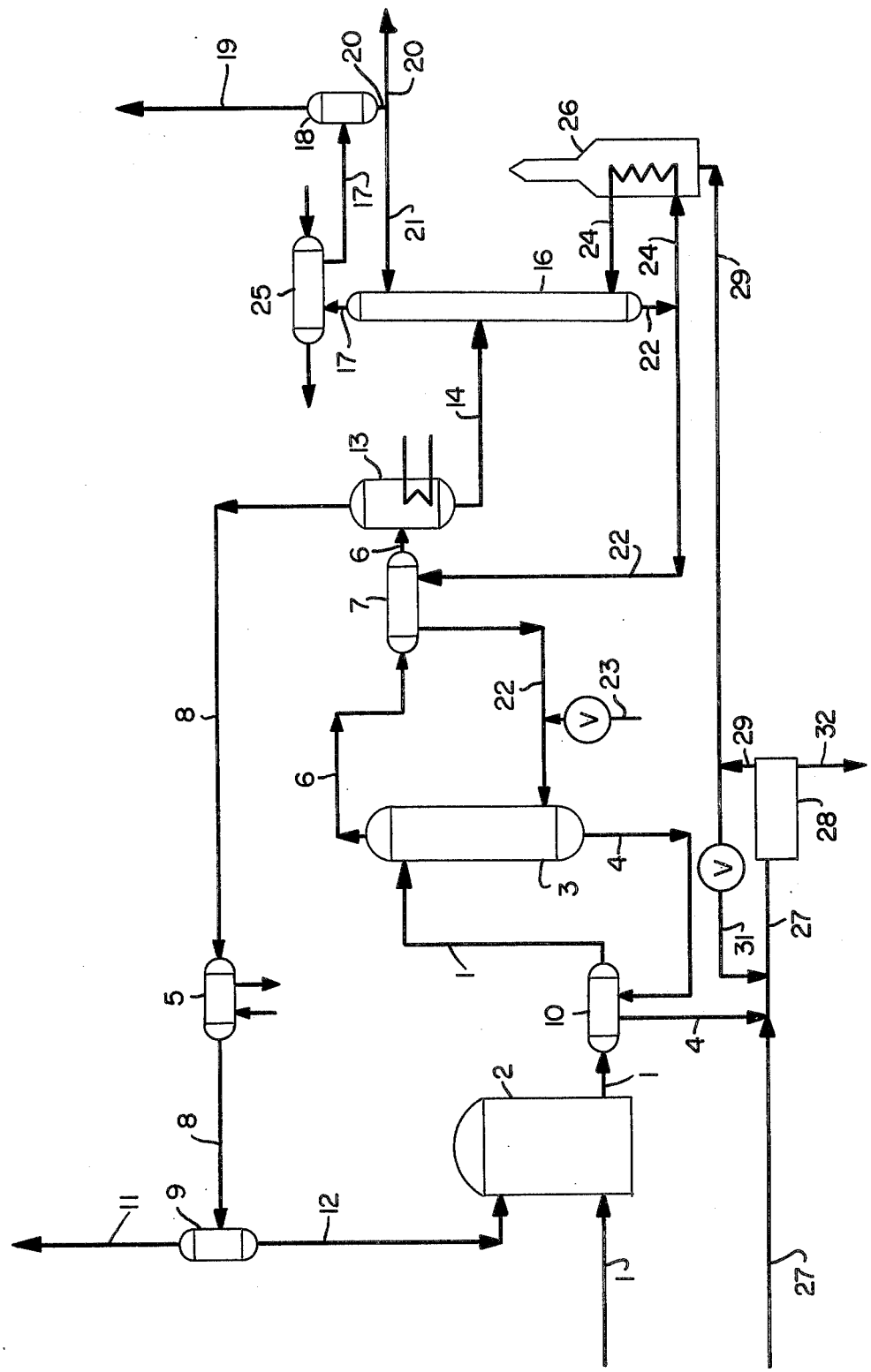

PROCESS FOR THE RECOVERY OF AMIDES

FIELD OF THE INVENTION

This invention relates to an improvement in a process for the recovery of amides from aqueous solutions and, more particularly, to a solvent extraction-distillation process therefor.

DESCRIPTION OF THE PRIOR ART

The recovery of water-soluble amides, particularly caprolactam, from aqueous solutions such as industrial waste water is especially significant in this era of shortages and pollution control since amides fall into that class of chemicals which are on one hand useful intermediates and on the other hand can pollute public waters if permitted access thereto. Many reclamation processes have been suggested and used to recover amides such as ordinary distillation and multiple batch evaporation, but the cost of bulk distillation is prohibitive from a commercial point of view and evaporation techniques, although not as expensive, do not have any special economic advantages in addition to which small amounts of amides cannot be separated at all by this technique. To overcome these shortcomings, solvent extraction was introduced and found to be the most desirable form of recovery; however, until now only low capacity solvents have been suggested. Further, prior art solvents had poor selectivity and, in many cases, vaporization of the solvent was required for the separation, a costly procedure.

SUMMARY OF THE INVENTION

An object of this invention, therefore, is to provide a liquid-liquid extraction process for the recovery of amides utilizing a high capacity, highly selective solvent while avoiding solvent vaporization.

Other objects and advantages will become apparent hereinafter.

According to the present invention, a solvent extraction-distillation process has been discovered in which water-soluble aliphatic amides having 1 to 8 carbon atoms or mixtures thereof are successfully recovered from an aqueous solution wherein the concentration of the amide is in the range of about 0.25 percent by weight to about 25 percent by weight, based on the weight of the solution, and the solvent is a compound having the following structural formula:

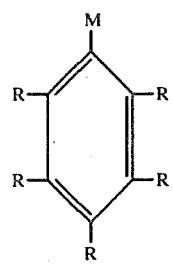

wherein M is OH or $CH_2OH$, R is hydrogen or an alkyl radical, there being at least one alkyl radical, and the total number of carbon atoms in all of said alkyl radicals taken together is 3 to 12, or a mixture of isomers thereof, said compound or mixture of isomers having a boiling point higher than the amide and less than about 350° C. and being nonazeotropic with the amide comprising the following steps:

(a) contacting the solution in an extraction zone with the solvent to provide an extract comprising solvent, amide, and no more than about 5 percent by weight of water based on the weight of the solution and a raffinate comprising at least about 95 percent by weight of water based on the weight of the solution and less than about 5 percent by weight of solvent based on the weight of the solvent;

(b) introducing the extract from step (a) into a distillation zone wherein the pressure is less than about 500 millimeters of mercury and the temperature is less than the decomposition temperature of the amide and solvent at said pressure, to separate the solvent from a mixture of amide and water; and (c) recovering the mixture of amide and water.

BRIEF DESCRIPTION OF THE DRAWING

The sole FIGURE is a schematic flow diagram of an illustrative embodiment of the present invention.

DESCRIPTION OF THE PREFERRED EMBODIMENT

As noted heretofore, the amide of particular interest in the instant recovery process is epsilon-caprolactam, which is useful in the manufacture of synthetic fibers such as nylon 6, plastics, bristles, film, coatings, synthetic leather, plasticizers, and paint vehicles, and as a cross-linking agent for curing polyurethanes. Examples of other water-soluble amides which can be recovered by the same process are formamide, acetamide, propionamide, n-butyramide, n-valeramide, N,N-dimethylacetamide, N,N-diethylacetamide, N-methyl-epsilon-caprolactam, 1,5-dimethyl-2-pyrrolidone, and 2-pyrrolidone. The term "water-soluble" as used herein means solubility at ambient temperatures. From the examples, it is clear that the water-soluble aliphatic amides contemplated here can be straight or branched chain or cyclic with or without alkyl substitution; further, the so-called cyclic amide in reality has a heterocyclic structure. Although inert substituents can be present in the various amide structures, only the alkyl substituent is preferred. The term "inert" as used here simply means that the substituent can pass through subject process without reaction or decomposition. Mixtures of the amides can also be recovered by the process, after which conventional separating techniques are applied to recover the individual amides. The amides of interest can also be characterized as those having boiling points in the range of about 200° to about 275° C.

The aqueous solution to which this process is applied has an amide concentration of about 0.25 percent by weight to about 25 percent by weight, based on the weight of the solution. The lower limit of about 0.25 percent will be recognized by those skilled in the art as an advantage of the present invention as it is an indication of the capacity and selectivity of the liquid extractive solvent. The upper limit of about 25 percent by weight, on the other hand, is an arbitrary limit of practicality above which the economics do not justify commercialization since ordinary distillation techniques will suffice. The preferred range of operation is from about 0.5 percent by weight to about 5 percent by weight of amide based on the weight of the aqueous solution.

Various impurities other than the defined amides can also be present in the solution provided that, as a practical matter, they are inert to the process components, do not have a substantial adverse affect on the capacity or selectivity of the solvent, and/or do not require any special separation technique. Such impurities can be present in the solution in the range of about 0.1 percent by weight or less to about 10 percent by weight based on the weight of the solution. Examples of these impurities are inorganic salts, alcohols, amines, hydrocarbons, etc.

The solvent selected for the instant process is, as set forth above, a compound having the following structural formula:

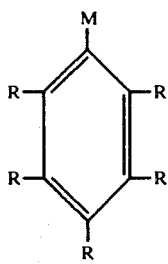

wherein M is OH or CH$_2$OH, R is hydrogen or an alkyl radical, and the total number of carbon atoms in all of said alkyl radicals taken together is 3 to 12, or a mixture of isomers thereof. Further, each compound or mixture of isomers has a boiling point higher than the amide to be recovered and less than about 350° C. In addition, the compound is non-azeotropic with the amide. Examples of the compounds are:

dodecylphenol
octylphenol
nonylphenol
2-Propylphenol
3-Propylphenol
4-Propylphenol
2-tert-Butylphenol
3-tert-Butylphenol
4-tert-Butylphenol
2-n-Butylphenol
3-n-Butylphenol
4-n-Butylphenol
2 Methyl-x-tert-Butylphenol
2-Methyl-y-tert-butylphenol
3-Methyl-x-tert-butylphenol
4-Methyl-2 tert-butylphenol
4-Methyl-2-sec- butylphenol
4-tert-Amylphenol
4-n-Amylphenol
2-Methyl-4-tert-amylphenol
3-Methyl-4-tert-amylphenol
4-Methyl-2-tert-amylphenol
2,3-Dimethyl-x-tert-butylphenol
2,3-Dimethyl-y-tert-butylphenol
2,4-Dimethyl-6-tert-butylphenol
2,5-Dimethyl-4-tert-butylphenol
2,6-Dimethyl-4-tert-butylphenol
3,4-Dimethyl-6-tert-Butylphenol
2-Ethyl-x-tert-butylphenol
2-Ethyl-4-tert-butylphenol
3-Ethyl-x-tert-butylphenol
4-Ethyl-2-tert-butylphenol
2-4-Di-tert-butylphenol
4-Diisobutylphenol
3-Methyl-4-diisobutylphenol
2-Methyl 4,6 -di-tert-butylphenol
3-Methyl 4,6 di-tert-butylphenol
4-Methyl-2,6 di-tert-butylphenol
2-Methyl-4-diisobutylphenol
4-Methyl-2-diisobutylphenol
2,3-Dimethyl-4,6-di-tert-butylphenol
2-Ethyl-4,6-di-tert-butylphenol
3-Ethyl 4,6 di-tert-butylphenol
4-Ethyl 2,6 di-tert-butylphenol
4-Methyl 2,6 di-tert amylphenol
2,4,6 Tri-tert-butylphenol
2-n-hexyl benzyl alcohol
3-tert-butyl benzyl alcohol
4-isoamyl benzyl alcohol
2,4-di-n-propyl benzyl alcohol
2,3,5-trimethyl benzyl alcohol
3-methyl-4-n butyl benzyl alcohol
2-methyl-4 tert-butyl benzyl alcohol It should be pointed out that the defined solvent compounds, as a group, have excellent thermal stability, an advantage during the distillation step. Mixed isomers are most commonly used rather than a single isomer since this is the way they are generally sold commercially. The preferred solvent is the mixed isomer of dodecylphenol although a single isomer would be just as satisfactory. The ring position of the alkyl radicals in the above examples of solvents have no particular significance in the instant process.

The amount of solvent needed to accomplish the extraction depends on the feedstock, i.e., the composition of the aqueous solution, and the particular solvent utilized. In practice, this is determined by the operator after analysis of the feedstock, extract, and raffinate. The optimum extract has, of course, the highest percentage of amide and the lowest percentage of water in terms of the original feedstock. Generally solvent to feed ratios on a parts by volume basis run in the range of about 0.05 part of solvent to about 1 part of solvent per part of feed (aqueous solution) and are preferably in the range of about 0.2 to about 0.5 part of solvent per part of feed. To repeat, the optimum amounts of solvent are determined by the technician and these ranges, especially the preferred range, can only serve as guidelines.

The apparatus used in the process both for extraction and distillation are conventional, e.g., an extraction column of the multistage reciprocating type containing a plurality of perforated plates centrally mounted on a vertical shaft driven by a motor in an oscillatory manner can be used as well as columns containing pumps with settling zones, sieve trays with upcomers, or even a hollow tube while the distillation can be conducted in a packed or bubble plate fractionating column. Counter-current flows are generally utilized in both extraction and distillation columns. Further, although single-stage extractions are illustrated hereinafter, multi-stage extractions can be availed of if desired. Feed tank, heat exchangers, water evaporator, heater, condensate drums, mixer-settler, vacuum system, and piping are also conventional.

A typical system in which subject process is used is described as follows: aqueous amide solution is introduced along line 1 and is stored in feed tank 2 to which is added through line 12 aqueous distillate containing some amide from a subsequent step. The aqueous solution continues along line 1 through heat exchanger 10 to recover heat from the extractor raffinate. The solution is heated to a temperature in the range of about 50° C. to about 150° C. in heat exchanger 10 and it then continues through line 1 to extractor 3 near the top. The solvent is introduced at the bottom of extractor 3 through line 22, any make-up solvent coming from an outside source through line 23. The aqueous solution passes down the column meeting and commingling with the solvent passing up the column, which extracts the amide from the solution. The extract leaves extractor 3 overhead through line 6. It is comprised of at least about 95 percent by weight of solvent based on the weight of the solvent introduced into the extractor; essentially all of the amide; and no more than about 5 percent by weight of water based on the weight of the aqueous solution introduced into the extractor. Preferably the solvent is at least about 98 percent and the water no more than about 3 percent.

The raffinate passes as bottoms through line 4 and is comprised of no less than about 95 percent by weight of water based on the weight of the aqueous solution and less than about 5 percent by weight of solvent based on the total weight of the solvent introduced into the extractor. Preferably, the water is no less than about 97 percent and the solvent is less than about 2 percent. The temperature of the raffinate at the bottom of the extractor is in the range of about 50° to about 150° C. The heat of the raffinate is recovered in heat exchanger 10 and the raffinate then passes into line 27, the liquid hydrocarbon fuel stream.

The extract passes through line 6 into heat exchanger 7 where it recovers heat from the solvent passing through line 22. The extract is heated to a temperature of about 75° to about 200° C in heat exchanger 7. It continues along line 6 into heated water evaporator 13, which is operated at a pressure of about 25 to about 760 millimeters of mercury and preferably about 50 to about 500 millimeters of mercury, where essentially all of the water is removed. The water containing a small amount of amide, about 1 to about 3 percent by weight based on the weight of the amide in the aqueous solution introduced into the system, passes through line 8 as aqueous distillate into heat exchanger 5 where it is condensed and then passes into condensate drum 9, from which the distillate is recycled along line 12 to feed tank 2. Heat is recovered in heat exchangers 5 and 25 and is optionally used in various parts of the system in order to economize on fuel. These connections are not shown in the drawing, however. The vacuum system (not shown) is connected to condensate drum 9 via line 11. The extract leaves water evaporator 13 as bottoms essentially devoid of water along line 14 and passes into the upper half of distillation column 16.

The distillation column is operated under sub-atmospheric pressure in the range of about 1 to about 500 millimeters of mercury and preferably at about 5 to about 250 millimeters of mercury.

The bottom temperature of both water evaporator 13, which is a form of distillation column, and distillation column 16 are operated at temperatures below the decomposition temperature of the particular solvent used at the particular pressure selected. With the above proviso, the water evaporator is generally, however, operated at a temperature in the range of about 75° to about 200° C. and the bottom temperature of distillation column 16 is kept above the boiling point of the amide, but well below the boiling point of the solvent. Where the boiling points permit, the bottoms temperature is below about 250° and preferably below 225° C. The temperature is controlled by circulating bottoms, which are essentially solvent, into line 22 to line 24, through heated reboiler 26 and back to the bottom of the still through line 24. The heated reboiler is fueled through line 29.

The overhead distillate, which is essentially amide, passes through line 17 into heat exchanger 25 where it is condensed. It then passes through line 17 into condensate drum 20, from which the amide passes as bottoms through line 25 and is recovered as product. A portion of the amide, however, is recycled via line 21 to distillation column 16 as reflux. The reflux ratios are in the range of about 0.1:1 to about 10:1. The vacuum system (not shown) is also connected to the described system through line 19.

The unrecycled portion of the still bottoms which is essentially solvent passes along line 22 to heat exchanger 7 where its heat is recovered and it then passes through line 22 returning to the extractor.

As noted, the aqueous raffinate leaves the bottom of extractor 3 via line 4. Its heat is recovered in heat exchanger 10 and it continues along line 4 where the raffinate joins the liquid hydrocarbon fuel passing through line 27. This combined stream passes into a single stage mixer-settler 28 where water is removed through line 32 and a mixture of fuel and solvent proceeds through line 29 to distillation column heater 26 where it is burned. A portion of the mixture, however, is recycled through lines 31 and 27 as an additional wash step. This treatment is only one way to remove the alkylphenol from the raffinate. Foam fractionation and charcoal filtration can also be used to remove alkylphenols from aqueous streams. The illustrated procedure is preferred, however, since it utilizes the solvent within the system very economically. An alternative to the illustrated procedure is to wash the raffinate in a single stage mixer-settler with a small amount of a light hydrocarbon preferably a hexanes-heptanes fraction. This hydrocarbon which now includes the small amount of solvent present in the raffinate can then be mixed with the bulk solvent phase in extractor 3. Thus, the fraction will also act as an entraining agent for water in water evaporator 13. While it is true that light aliphatics are generally not completely miscible with alkylphenols or alkylbenzyl alcohols and mixing them with the bulk solvent phase in the extractor could form a third liquid phase, which could seriously hamper the operation of the extractor, the defined alkylphenols used in subject process avoid this problem.

It should be noted that the use of water evaporator 13 is an alternative mode of operation and depends on the desired result. Where amide essentially free of water is required the water evaporator is the best choice. Where a high percentage of water is permissible in the product, e.g., up to about 5 percent by weight based on the weight of the feedstock, the water evaporator can be eliminated and the process conducted as otherwise illustrated. Where an intermediate amount of water is acceptable, this can be handled by fractional distillation. In the latter two cases, still 16 is used above to separate the solvent from the mixture of amide and water. In the former case, water evaporator 13, which is, in effect a still, and distillation column 16 operate in tandem to accomplish the separation. To repeat, these are alternative procedures.

The following examples illustrate the invention:

EXAMPLE 1

Subject process is carried out according to the preferred embodiment, the typical system, and the drawing as heretofore described.

The aqueous solution (100 parts by weight) contains 2 percent by weight epsilon-caprolactam. The solvent (a mixture of dodecylphenol isomers) to feed ratio by volume is 0.2/1. The extractor, a 2 inch diameter column having 2.8 theoretical trays, is operated at a temperature of 80° C and a pressure of 1 atmosphere at the top of the column. The water evaporator is operated at a temperature of 136° C, and a pressure of 100 mm.Hg. The distillation column is a one-inch diameter column having 30 sieve plates. It is operated at a bottoms temperature of 188° C., a pressure of 10 millimeters of mercury, and a 4/1 reflux ratio. 99 Weight percent of the epsilon-caprolactam is recovered and it has a freezing point of 69.0° C corresponding to very high purity epsilon-caprolactam.

Analysis shows that the extract from the extractor contains 2 percent by weight water based on the weight of the aqueous solution; the raffinate from the extractor contains 98 percent by weight water based on the weight of the solution and one percent solvent based on the weight of the solvent introduced into the extraction; essentially all of the water is removed overhead from the water evaporator and contains 1 percent by weight of the amide in the initial aqueous solution.

EXAMPLE 2

Example 1 is repeated using as solvent 2-n-hexyl benzyl alcohol. The results are similar to those in Example 1.

I claim:

1. A solvent extraction-distillation process for the recovery of a water-soluble amide selected from the group consisting of an aliphatic amide having 1 to 8 carbon atoms, epsilon-caprolactam, N-methyl-epsilon-caprolactam, 1,5-dimethyl-2-pyrrolidone, 2-pyrrolidone and mixtures thereof, from an aqueous solution thereof wherein the concentration of the amide is in the range of about 0.25 percent by weight to about 25 percent by weight, based on the weight of the solution, and the solvent is a compound having the following structural formula:

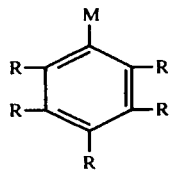

wherein M is OH or $CH_2OH$, R is hydrogen or an alkyl radical, there being at least one alkyl radical, and the total number of carbon atoms in all of said alkyl radicals taken together is 3 to 12, or a mixture of isomers thereof, said compound or mixture of isomers having a boiling point higher than the amide and less than about 350° C. and being non-azeotropic with the amide, comprising the following steps:

a. contacting the aqueous solution of said amide in an extraction zone with the solvent in a solvent to aqueous solution feed ratio of from about 0.05 to about 1 part by volume of solvent per part by volume of aqueous solution, to provide an extract comprising solvent, amide, and no more than about 5 percent by weight of water based on the weight of the solution, and a raffinate comprising at least about 95 percent by weight of water based on the weight of the solution and less than about 5 percent by weight of solvent based on the weight of the solvent;

b. introducing the extract from step (a) into a distillation zone, wherein the pressure is less than about 500 millimeters of mercury and the temperature is less than the decomposition temperatures of the amide and the solvent at said pressure, to separate the solvent from a mixture of amide and water; and c. recovering the mixture of amide and water.

2. A solvent extraction-distillation process for the recovery of a water-soluble amide selected from the group consisting of an aliphatic amide having 1 to 8 carbon atoms, epsilon-caprolactam, N-methyl-epsilon-caprolactam, 1,5-dimethyl-2-pyrrolidone, 2-pyrrolidone and mixtures thereof, from an aqueous solution wherein the concentration of the amide is in the range of about 0.25 percent by weight to about 25 percent by weight, based on the weight of the solution, and the solvent is a compound having the following structural formula:

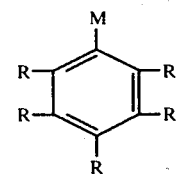

wherein M is OH or $CH_2OH$, R is hydrogen or an alkyl radical, there being at least one alkyl and the total number of carbon atoms in all of said alkyl radicals taken together is 3 to 12, or a mixture of isomers thereof, said compound or mixture of isomers having a boiling point higher than the amide and less than about 350° C. and being non-azeotropic with the amide, comprising the following steps:

a. contacting the aqueous solution of said amide in an extraction zone with the solvent in a solvent to aqueous solution feed ratio of from about 0.05 to about 1 part by volume of solvent per part by volume of aqueous solution, to provide an extract comprising solvent, amide, and no more than about 5 percent by weight of water based on the weight of the solution and a raffinate comprising at least about 95 percent by weight of water based on the weight of the solution and less than about 5 percent by weight of solvent based on the weight of the solvent;

b. introducing the extract from step (a) into a first distillation zone, wherein the pressure is no greater than about 760 millimeters of mercury and the temperature is less than the decomposition temperatures of the amide and the solvent at said pressure, to separate the water from a mixture of amide and solvent;

c. introducing the mixture of amide and solvent from step (b) into a second distillation zone, wherein the pressure is less than about 500 millimeters of mercury and the temperature is less than the decomposition temperatures of the amide and the solvent at said pressure, to separate the amide from the solvent; and d. recovering the amide.

3. The process defined in claim 1 wherein the concentration of the amide is in the range of about 0.5 percent to about 5 percent; the extract of step (a) contains no more than about 3 percent water; the raffinate of step (a) contains at least about 97 percent water and less than about 2 percent solvent; and the pressure in step (b) is in the range of about 5 to about 250 millimeters of mercury.

4. The process defined in claim 2 wherein the concentration of the amide is in the range of about 0.5 percent to about 5 percent; the extract of step (a) contains no more than 3 percent water; the raffinate of step (a) contains at least about 97 percent water and less than about 2 percent solvent; and the pressure in step (c) is in the range of about 5 to about 250 millimeters of mercury.

5. The process defined in claim 3 wherein the amide is epsilon-caprolactam.

6. The process defined in claim 4 wherein the amide is epsilon-caprolactam.

7. The process defined in claim 5 wherein the solvent is a mixture of isomers of dodecylphenol.

8. The process defined in claim 6 wherein the solvent is a mixture of isomers of dodecylphenol.

9. A solvent extraction-distillation process for the recovery of epsilon-caprolactam from an aqueous solution thereof wherein the concentration of epsilon-caprolactam is in the range of about 0.25 percent by weight to about 25 percent by weight, based on the weight of the solution, and the solvent is dodecylphenol, which comprises the following steps:

a. introducing dodecylphenol and the aqueous solution of epsilon-caprolactam to an extraction zone at a volumetric ratio from about 0.05 to about 1 part of dodecylphenol per part of aqueous solution of epsilon-caprolactam, in said extraction zone contacting the aqueous solution of epsilon-caprolactam with dodecylphenol to provide an extract comprising dodecylphenol, epsilon-caprolactam and no more than about 5 percent by weight of water based on the weight of said aqueous solution of epsilon-caprolactam, and a raffinate comprising at least about 95 percent by weight of water based on the weight of said aqueous solution of epsilon-caprolactam and less than about 5 percent by weight of dodecylphenol based on the total weight of dodecylphenol fed to the extraction zone;

b. introducing the mixture of epsilon-caprolactam and dodecylphenol from step (a) into a distillation zone wherein the pressure is less than about 500 millimeters of mercury and the temperature is less than the decomposition temperatures of the epsilon-caprolactam and dodecylphenol at said pressure, to separate epsilon-caprolactam from the dodecylphenol; and c. recovering the epsilon-caprolactam.

10. The process defined in claim 9 wherein the volumetric ratio of the dodecylphenol and aqueous solution of epsilon-caprolactam fed to the extraction zone is no more than about 0.5 part of dodecylphenol per part of said aqueous solution.

* * * * *